United States Patent [19]
Pagano

[11] Patent Number: 6,088,427
[45] Date of Patent: Jul. 11, 2000

[54] APPARATUS FOR RADIOLOGICAL EXAMINATION HAVING A RECIPROCATING GRID PROVIDED WITH A COUNTERWEIGHT

[75] Inventor: Gaetano Pagano, Florence, Italy

[73] Assignee: Maria Pagano, Varese, Italy

[21] Appl. No.: 09/179,692

[22] Filed: Oct. 27, 1998

[30] Foreign Application Priority Data

Oct. 28, 1997 [IT] Italy .................................. PN97A 0059

[51] Int. Cl.[7] ...................................................... G21K 1/00
[52] U.S. Cl. ........................................... 378/155; 378/154
[58] Field of Search ...................................... 378/155, 154

Primary Examiner—Craig E. Church
Attorney, Agent, or Firm—Wenderoth, Lind & Ponack, L.L.P.

[57] ABSTRACT

An apparatus for radiological examination is provided with the grid 16 that is driven in reciprocating motion in order to reduce the effect of radiation scattered by the body of the patient being irradiated. The grid 16 is connected to a counterweight 23, and is moved through a motion transmission mechanism that is of the crank and connecting-rod type so as to ensure a dynamic balancing of the oscillating masses. With this simple and accurate type of driving system, better quality radiographic images can be obtained under different adjustment and set-up conditions of the apparatus.

19 Claims, 6 Drawing Sheets

APPARATUS FOR RADIOLOGICAL EXAMINATION HAVING A RECIPROCATING GRID PROVIDED WITH A COUNTERWEIGHT

BACKGROUND OF THE INVENTION

The present invention relates to apparatuses for radiological examination, and particularly to the portion of such apparatuses used to hold photographic film or plates onto which the image of a part of the body of the patient that is undergoing examination is impressed.

Radiology is commonly known as the medical science that is concerned with the use of ionizing radiation, particularly x-rays, for the purpose of diagnosis and treatment of disease. A part of the body of the patient is substantially exposed to a beam of radiation that moves through the body in a selective manner, and finally impresses an image on the photographic film. An image is thereby provided from which valuable clinical information can be derived concerning the part of the body undergoing examination.

A major problem that is encountered in connection with radiological examination is the scattering of radiation in the body of the patient, which scattering gives rise to interference on the image. That is, the image is intended to be generated by direct radiation, but indirect radiation due to scattering can interfere with this image. As a result, radiological apparatus require the provision of an arrangement that enables the apparatus to minimize the effect of scattered radiation. Such an arrangement is generally known in the art as a Potter-Bucky grid, or a Bucky diaphragm. In practical terms, this is a grid that is formed by an assembly of lead strips, resembling an open Venetian blind, which is placed between the body of the patient that is being x-rayed and the photographic film or plate that is to receive the image. The grid has the task of filtering out the scattered radiation that would otherwise impair the quality of the impressed image.

The rectilinear lead strips of the grid are usually spaced from each other by the interposition of strip of an x-ray transparent material. In the past this was usually wood, but is now commonly replaced by plastics or aluminum. The lead strips are oriented so that they are directed towards a virtual line, that is, the focal line. The focus of the x-ray emitting tube is placed along this focal line. The primary rays, after having passed through the body of the patient, come up against the grid. The strips of the grid oppose the primary rays at just a minimum of the overall absorption surface. Conversely, oblique rays due to scattering by the body of the patient are prevented from passing through the grid by the strips. Thus, the grid carries out selective absorption of the scattered radiation.

Moving grids were first provided by assembling the strips in accordance with the cylindrical surface whose axis coincided with the focal line. During the movement of the grid, the grid remained focused. However, this particular type of embodiment had a major drawback in that examination tables were provided with a cylindrical surface having the grid placed thereunder, or if the surface was plane, in a preferable embodiment, the need arises to place the grid above the surface, having appropriate devices on all sides thereof for the convenience of the patient.

Currently, plane grids are used, which represents major progress. However, these plane grids still have drawbacks in that the focusing of the radiation is not maintained over all of the grid during movement.

The ratio of the height h of a lead strip to the distance d of the lead strip can be said to be R, and equal to h/d. A grid having a high ratio R requires the central ray to be focused in an extremely accurate manner. A centering or focusing error would in fact entail a considerable absorption effect. For example, a two degree focusing error on the grid having a ratio R of 6.5 would entail a 64% transmission for the primary radiation, whereas such a transmission would be further reduced to 37% with a ratio R of 16. In practice, there is a limit to the ratio R for the grids, the limit being set by the need for an acceptable compromise between the anti-scattering effect desired and the highest possible contrast which can be reached.

Another problem that has been encountered in using grids relates to the cancellation of the radiographic image of the grid itself. In order to cancel this image, the grid has been installed in a driving mechanism which confers a reciprocating motion to the grid. It is has been experimentally found that there are reciprocating speeds of the grid that bring about stroboscopic effects for displacements of a step or half a step. An appropriate selection of the speed, in accordance with the exposure time, enables such effects to be avoided, or at least to be minimized to negligible levels. It can be conclusively stated, however, that an overall solution of all of the afore mentioned problems and drawbacks relating to the use of grids has up to now proven to be practically impossible.

SUMMARY OF THE INVENTION

Accordingly, it is a main purpose of the present invention to provide an apparatus for radiological examination in which a support arrangement for a moving grid is driven in a simple and accurate manner so as to ensure a good radiographic image under different adjustments and set-up conditions of the apparatus.

The object according to the present invention is achieved by an apparatus for radiological examination which has a radiation source for producing radiation to be directed toward a patient, a holder for holding a film or plate and receiving radiation from the radiation source that is passed through a patient, and a grid. The grid includes an assembly of lead strips located between the radiation source and the film holder. The grid is mounted for reciprocating motion in a direction that is generally perpendicular to the direction from the radiation source to the film holder. A motor is connected to the grid for displacing the grid with reciprocating motion, the grid having an oscillating mass when in motion. A counterweight is connected so as to dynamically balance the oscillating mass of the grid during the reciprocating motion of the grid.

The motor preferably comprises a stepper motor. Furthermore, a first crank and a first connecting rod are preferably used to connect the motor to the grid. The counterweight, furthermore, is preferably connected to the motor by a second crank and a second connecting rod. The first and second cranks are preferably parallel with each other so as to be 180 degrees out of phase with each other.

An electronic control means is preferably provided in order to control the angular speed of the stepper motor. A housing supports the holder, mounts the grid for reciprocating motion and houses the motor and the counterweight. The electronic control means, furthermore, can control the stepper motor so as to maintain a constant reciprocating speed of the grid.

BRIEF DESCRIPTION OF THE DRAWINGS

Further objects, features and advantages of the present invention will become apparent from the following description of the preferred embodiment thereof, presented by way of nonlimiting example, and with reference to the accompanying drawings, in which.

DETAILED DESCRIPTION OF THE PREFERRED EMBODIMENT

Figure 1:
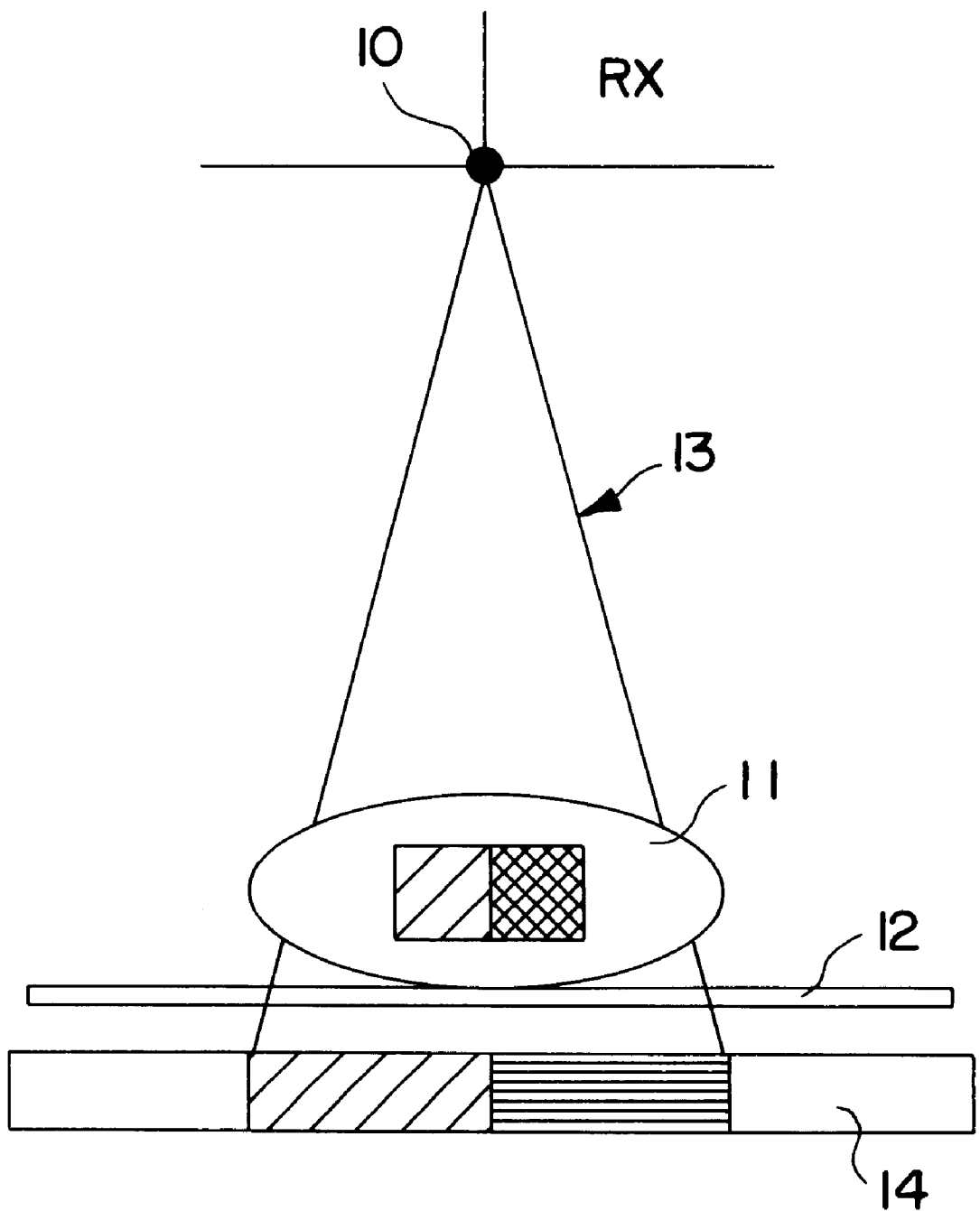
FIG. 1 is a schematic drawing illustrating the operating principles of an apparatus for radiological examination according to the present invention.
Figure 2:
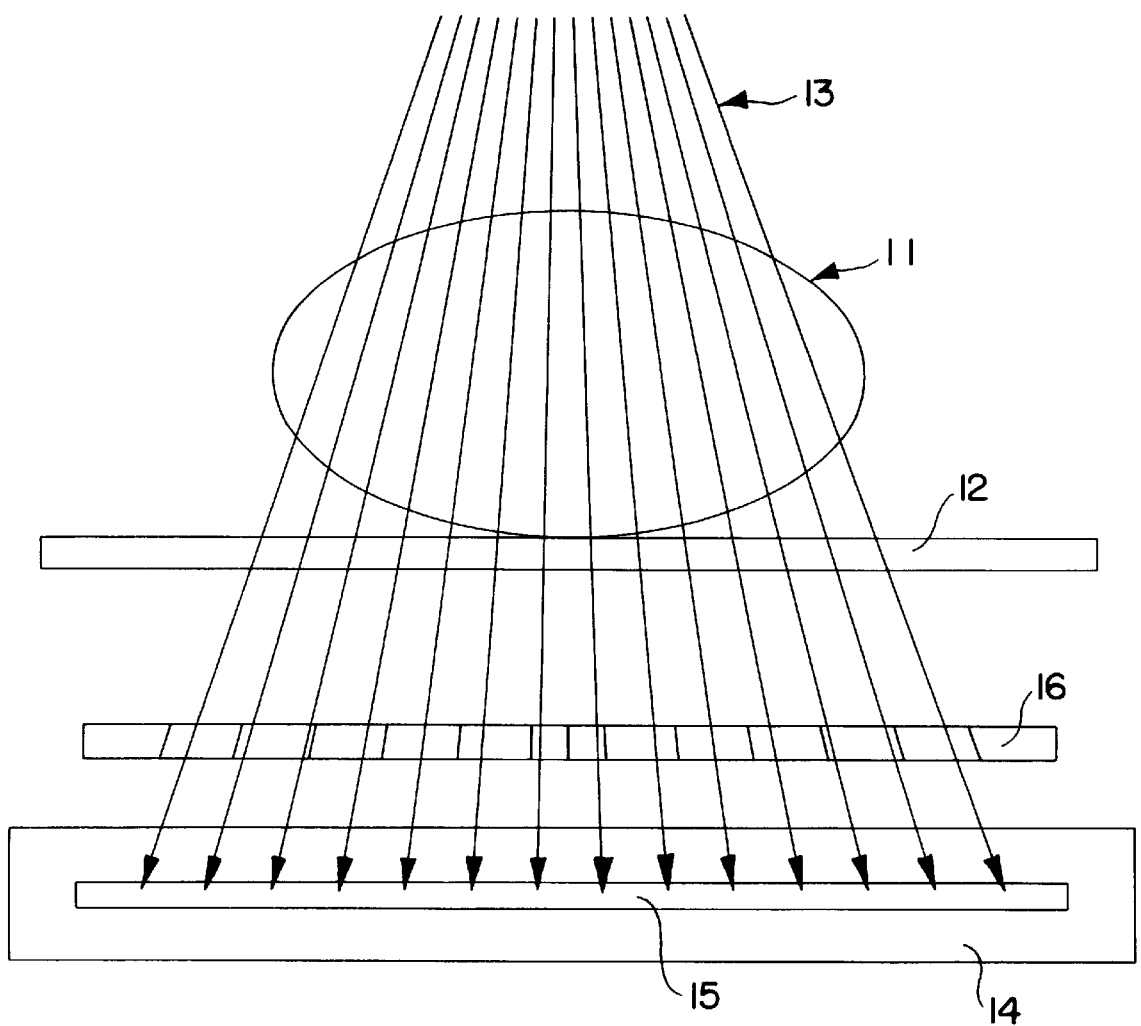
FIG. 2 is a view similar to FIG. 1, but showing details of the apparatus according to the present invention.

As is shown schematically in FIGS. 1 and 2, an apparatus for radiological examination generally includes a radiation source 10 which is preferably and typically an x-ray generator. Radiation 13 is directed towards the body of a patient 11 lying on an appropriate examination table 12. The radiation 13, after having passed through the body of the patient, reaches an arrangement 14 which includes a holder for a film or plate 15 that is to be impressed with an image. The arrangement 14 further includes a grid that is formed by lead strips 16 separated from each other by elements of an x-ray transparent material. The grid is displaced in a reciprocating motion by an appropriate driving mechanism when the apparatus is operating.

The grid 16 performs the task of filtering the x-rays scattered by the irradiated elements, i.e. the patient. Because such scattered rays would affect the quality of the image that is impressed on the photographic film or plate, it is desired to have them filtered. In order to ensure a good radiographic image, the reciprocating motion of the grid must, as far as possible, occur at a constant speed.

However, the grid 16, caused to be displaced with a reciprocating motion, can give rise, due to its mass, to vibrations over the entirety of the apparatus. As a result, this can contribute to lowering the quality of the attainable radiographic image. It would also cause a further inconvenience to the patient, who is usually lying quite close to the arrangement 14 that is receiving the image.

In order to eliminate such drawbacks, the present invention provides a counterweight for balancing the oscillating mass of the grid 16. According to a further preferred feature of the present invention, a stepper motor is used as the driving means for the grid and the counterweight, crank-connecting rod mechanisms are used as motion transmission mechanisms between the motor and the grid as well as the counterweight, and a power electronic control arrangement is provided for the stepper motor. This will be explained in further detail below.

Figure 5:
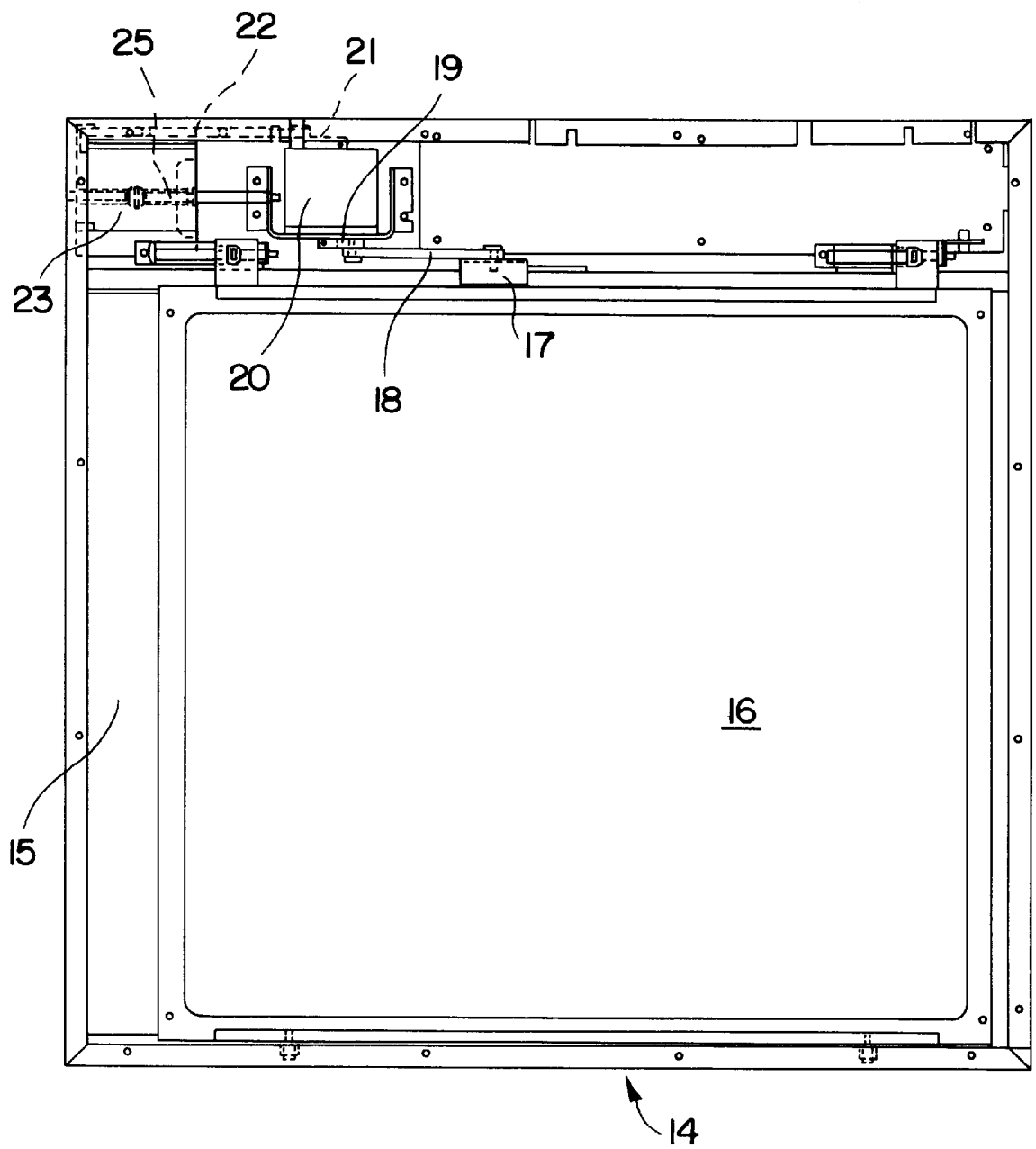
FIG. 5 is a schematic illustration of the apparatus for radiological examination according to the present invention as seen from the top.
Figure 6:
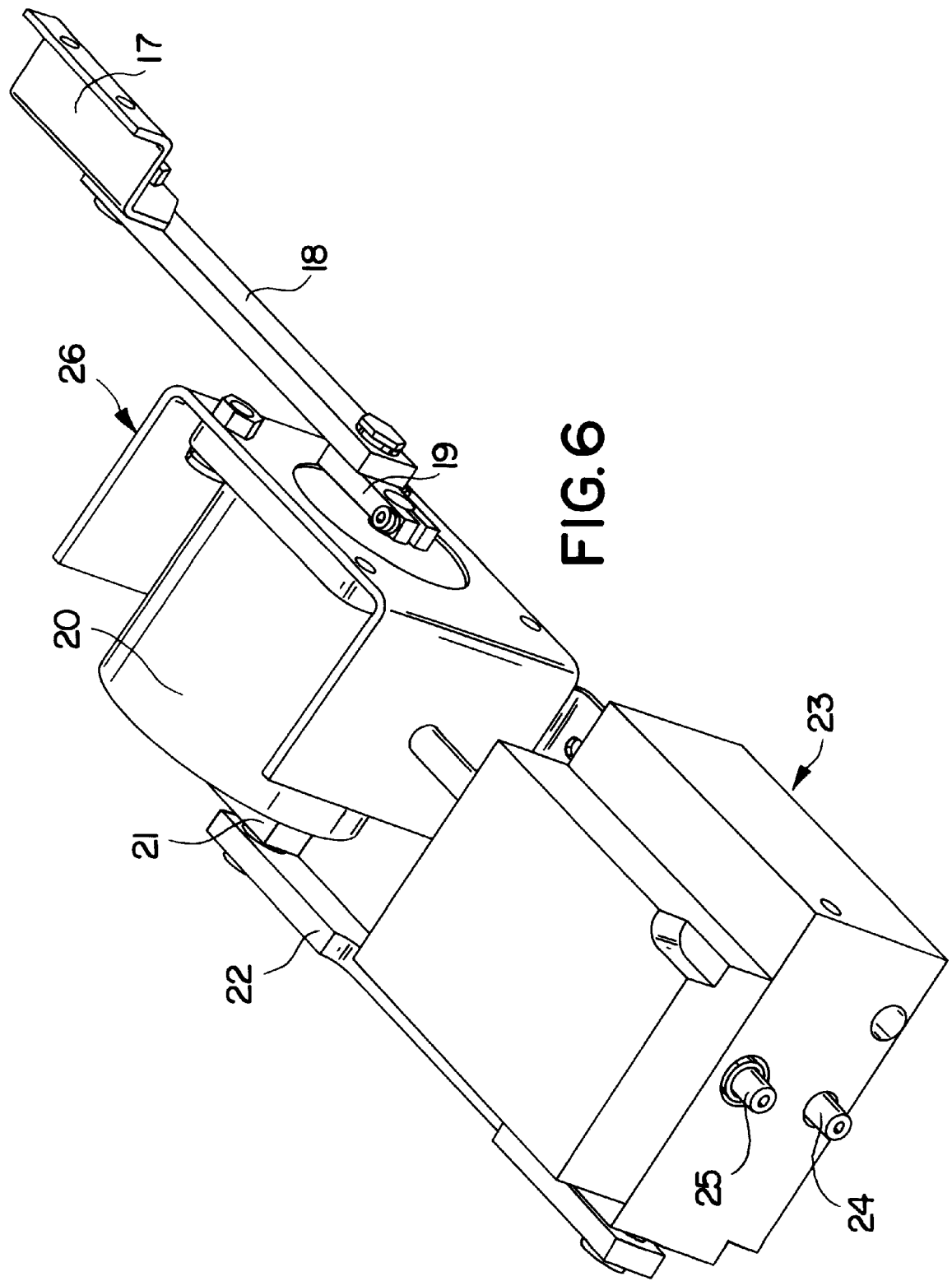
FIG. 6 is a perspective view of a detail of the apparatus illustrated in FIG. 5.

Turning to FIGS. 5 and 6, the arrangement 14 including the holder for holding the film or plate 15 to be impressed with the image and the moving grid 16 is housed in a box-like structure on a side of which the components of the present invention are assembled. The grid 16 is provided with a bracket 17. An end portion of a connecting rod 18 is pivotally connected with the bracket 17, and the other end of the connecting rod is pivotally attached to a crank 19. The crank 19 is also connected to an end portion of a shaft of a stepper motor 20.

At the other end of the shaft of the stepper motor 20 is connected a crank 21. A connecting rod 22 is pivotally connected to the crank 21 at one end thereof, and at the other end thereof is pivotally connected to a counterweight 23. The counterweight 23 is adapted to balance the mass of the grid 16 in its reciprocating motion. The cranks 19 and 21 of the respective motion transmission mechanisms from the motor to the grid and the counterweight are, preferably, provided so as to be parallel and out of phase, i.e. out of phase by 180 degrees.

With the above structure, accordingly, the counterweight 23 is displaced with a rectilinear reciprocating motion in opposite phase to the grid 16. It should be noted that the counterweight 23 is preferably guided in motion by two shafts 24 and 25 that are connected as end portions thereof to a support 26 of the stepper motor 20 and the chassy of the arrangement 14, respectively. Thus, the counterweight is able to rectilinearly slide on the support shafts 24 and 25.

Figure 3:
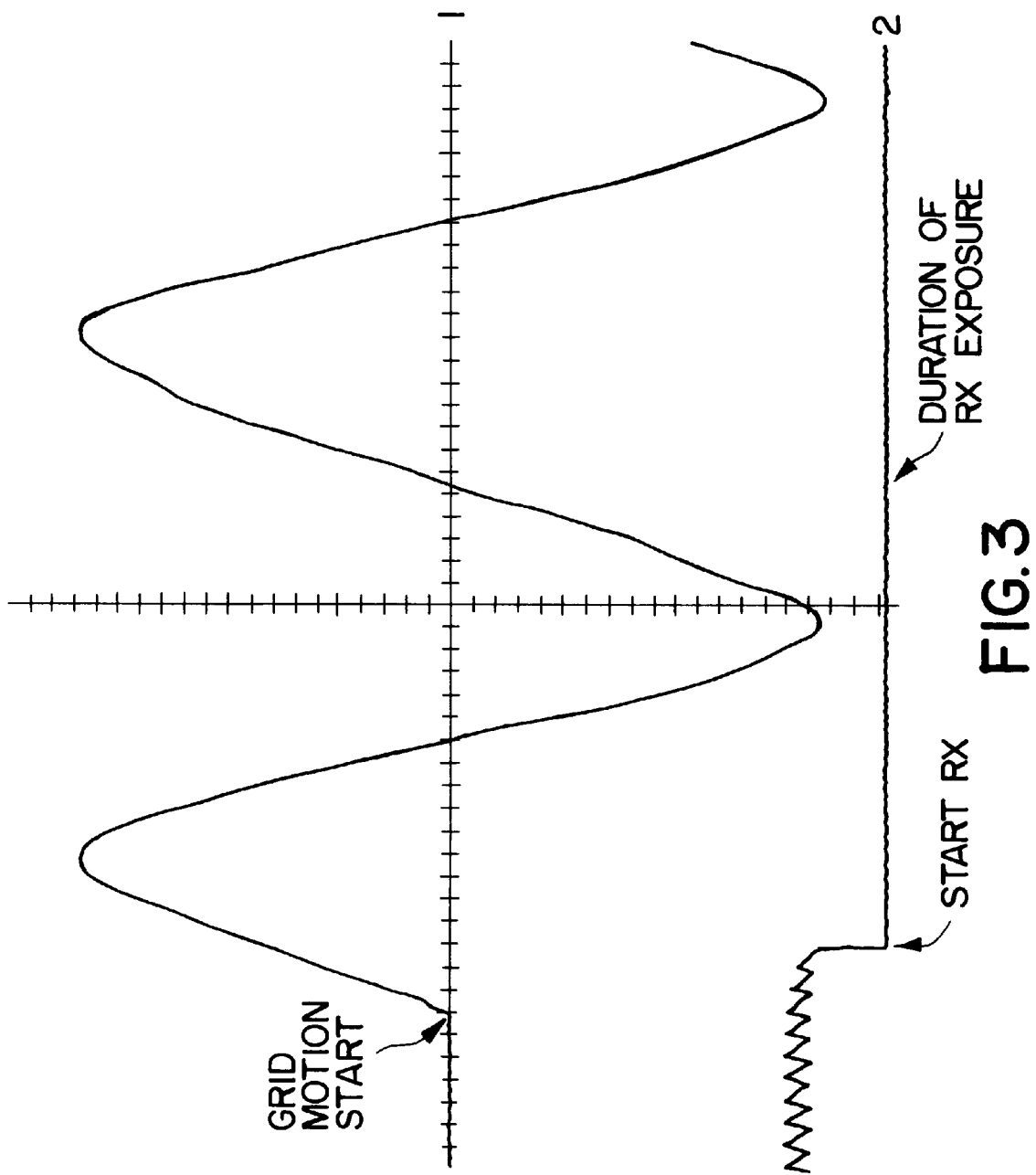
FIG. 3 is a diagram showing time versus speed for a displacement curve corresponding to a crank and connecting-rod mechanism for a grid connected with a motor without any speed adjustment provision.

The stepper motor 20 ideally turns at a constant speed. If it turns at a constant speed, the curve of the reciprocating displacement speed of the grid 16, due to the law governing the motion of oscillating masses, will have a sinusoidal profile as illustrated in FIG. 3. With the apparatus according to the present invention, programmable profiles can, on the contrary, be obtained for the reciprocating speed of the grid 16 in view of the elimination of the imbalances that were in the past brought about by inertial forces.

Figure 4:
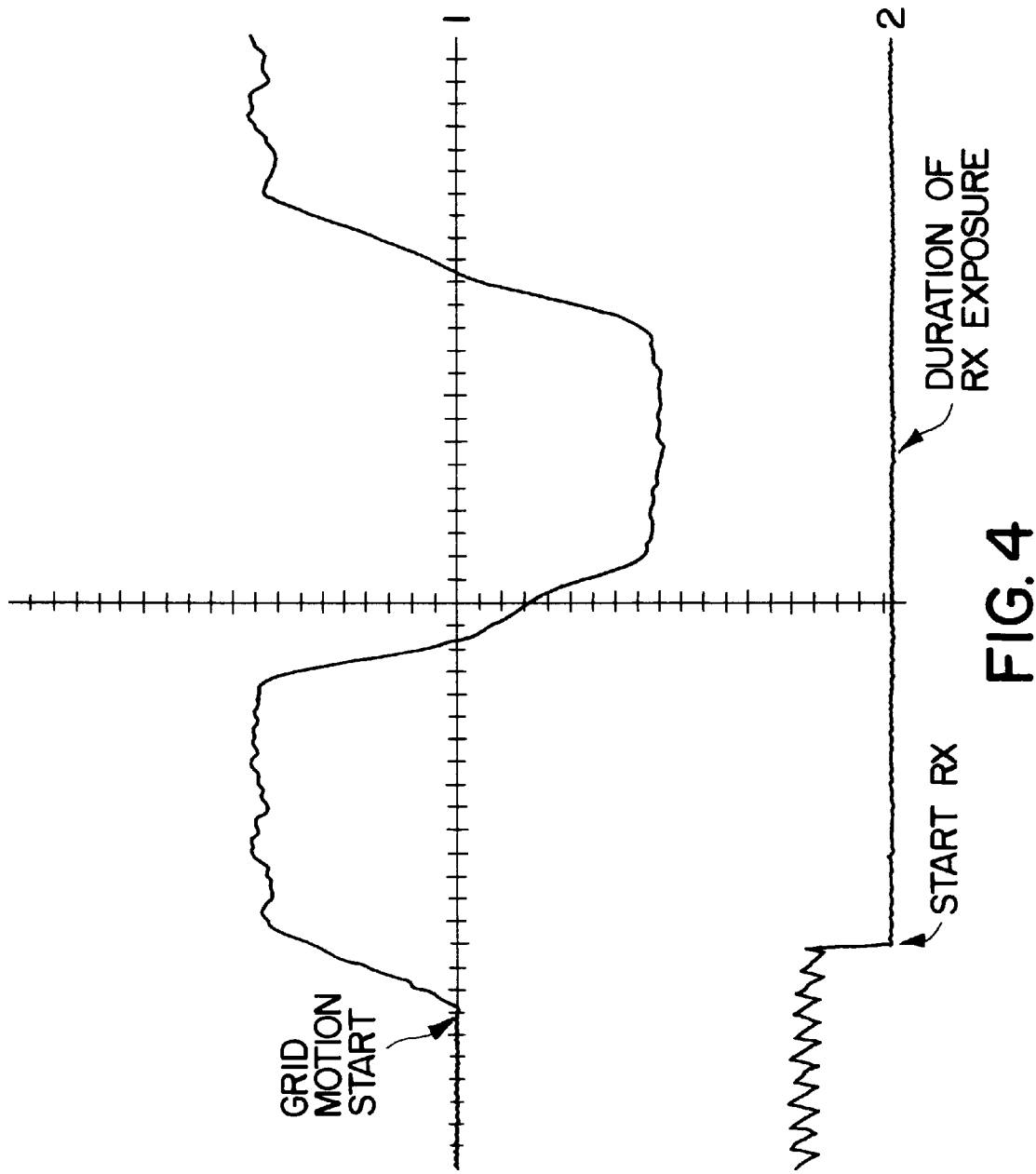
FIG. 4 is a diagram similar to that of FIG. 3, but demonstrating the use of instantaneous speed control for a driving motor in accordance with the present invention.

For a profile to be obtained which differs from the sinusoidal profile as shown in FIG. 3, the angular speed of the motor needs to be varied on an instant-by-instant basis in accordance with the rotation angle of the crank 19 and the speed profile that is desired to be obtained for the oscillating mass. One such profile is illustrated in FIG. 4. The variation in the angular speed of the motor is obtained by varying the times elapsing between two successive steps of the stepper motor 20. Such times are delivered to the power control unit of the motor by a microprocessor based control arrangement (which is of a per se known type, and, therefore, not illustrated). As a result, the sinusoidal pattern of the reciprocating speed of the grid 16 which is ordinarily brought about by the crank and connecting-rod type of motion transmission mechanism can be compensated for by control of the motor to provide for a constant speed of the grid 16.

I claim:

1. An apparatus for radiological examination, comprising:
   a radiation source;
   a holder for receiving radiation from said radiation source;
   a grid comprising an assembly of lead strips between said radiation source and said holder, said grid being capable of reciprocating motion;
   a motor capable of displacing said grid in reciprocating motion, said grid having an oscillating mass when in motion; and
   a counterweight balancing the oscillating mass of said grid.

2. The apparatus of claim 1, wherein said motor comprises a stepper motor, a first crank connected to said stepper motor and a connecting rod connected between said first crank and said grid.

3. The apparatus of claim 2, wherein said counterweight is driven by said stepper motor by a second crank connected to said stepper motor and a second connecting rod connected between said crank and said counterweight.

4. The apparatus of claim 3, wherein said first crank and said second crank are pivotally attached to a shaft of said stepper motor so as to be parallel with each other.

5. The apparatus of claim 4, wherein said stepper motor is controlled by an electronic control means for controlling the angular speed of said stepper motor.

6. The apparatus of claim 1, wherein said counterweight is driven by said motor by a crank connected to said motor and a connecting rod connected between said crank and said counterweight.

7. The apparatus of claim 6, wherein said motor is controlled by an electronic control means for controlling the angular speed of said motor.

8. The apparatus of claim 1, wherein said motor is controlled by an electronic control means for controlling the angular speed of said motor.

9. An apparatus for radiological examinations, comprising:

a radiation source for producing radiation to be directed toward a patient;

a holder for holding a film or plate and receiving radiation from said radiation source that has passed through a patient;

a grid comprising an assembly of lead strips located between said radiation source and said holder, said grid being mounted for reciprocating motion in a direction generally perpendicular to the direction from said radiation source to said holder;

a motor connected to said grid for displacing said grid with reciprocating motion, said grid having an oscillating mass when in motion; and a counterweight connected so as to dynamically balance the oscillating mass of said grid during reciprocating motion of said grid.

10. The apparatus of claim 9, wherein said grid and said counterweight are connected to a shaft of said motor so as to be 180 degrees out of phase with respect to each other.

11. The apparatus of claim 9, wherein said grid and said counterweight are connected to said motor with respective first and second motion transmission mechanisms.

12. The apparatus of claim 11, wherein said first and second motion transmission mechanisms each comprises a crank and a connecting rod.

13. The apparatus of claim 9, wherein said counterweight is mounted to reciprocate in a direction opposite to a direction of reciprocation of said grid.

14. The apparatus of claim 9, wherein a housing supports said holder, mounts said grid for reciprocating motion, and houses said motor and said counterweight.

15. The apparatus of claim 9, wherein said motor is a stepper motor.

16. The apparatus of claim 15, and further comprising an electronic control means for controlling the angular speed of said stepper motor.

17. The apparatus of claim 16, wherein said electronic control means controls said stepper motor so maintain a constant reciprocating speed of said grid.

18. The apparatus of claim 9, and further comprising an electronic control means for controlling the angular speed of said motor.

19. The apparatus of claim 18, wherein said electronic control means controls said motor so maintain a constant reciprocating speed of said grid.

* * * * *